(12) United States Patent
Yingling et al.

(10) Patent No.: US 7,348,159 B2
(45) Date of Patent: Mar. 25, 2008

(54) METHODS FOR DETERMINING PHOSPHORYLTRANSFERASE ACTIVITY USING ADENOSINE 5'-TRIPHOSPHATE (ATP)-GAMMA-S

(75) Inventors: Jeffrey David Yingling, Apex, NC (US); Scott Jakes, Southbury, CT (US); Donna Terenzio, Fairfield, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 194 days.

(21) Appl. No.: 11/110,435

(22) Filed: Apr. 20, 2005

(65) Prior Publication Data

US 2006/0240499 A1 Oct. 26, 2006

(51) Int. Cl.
*C12Q 1/48* (2006.01)

(52) U.S. Cl. .............................. 435/15; 435/8; 435/21

(58) Field of Classification Search .................. 435/15, 435/21, 8
See application file for complete search history.

(56) References Cited

U.S. PATENT DOCUMENTS 6,599,711 B2 * 7/2003 Crouch et al. ................ 435/15
2002/0172991 A1 11/2002 Crouch et al.

FOREIGN PATENT DOCUMENTS

EP 1233060 A2 8/2002

OTHER PUBLICATIONS

Kashem M et al. New Tools For Screening Protein Kinases. The Society for Biomolecular Screening 9th Annual Conference. Sep. 21-25, 2003, Portland Oregon.*
Jeong S. et al. Kinase Assay Based on Thiophosphorylation of Biotinylation. BioTechniques 27(6)1232-8, Dec. 1999.*
Chen, et al; Kinetic mechanism of the p38-alpha MAP kinase: phosphoryl transfer to synthetic peptides; Biochemistry; Feb. 29, 2000; vol. 39, No. 8; pp. 2079-2087.
Ward, et al; The intrinsic ATPase activity of protein kinase C is catalyzed at the active site of the enzyme; Biochemistry; Jun. 30, 1992; vol. 31, No. 25; pp. 5905-5911.
Dipolo, et al; In squid axons, ATP modulates Na+-Ca2+ exchange by a Ca2+i-dependent phosphorylation; Biochimica et Biophysica Acta; Mar. 12, 1987; vol. 897, No. 3; pp. 347-354.
Porrello, et al; Regulation of reactivated contraction in teleost retinal cone models by calcium and cyclic adenosine monophosphate; The Journal of Cell Biology; Jun. 1984; vol. 98, No. 6; pp. 2230-2238.
Cassidy, et al; Irreversible thiophosphorylation and activation of tension in functionally skinned rabbit ileum strips by [35S]ATP gamma S; The Journal of Biological Chemistry; Nov. 10, 1979; vol. 254, No. 21; pp. 11148-11153.
International Search Report for PCT/US2006/014860, 2006.

* cited by examiner

*Primary Examiner*—Ralph Gitomer
(74) *Attorney, Agent, or Firm*—Michael P. Morris; Mary-Ellen M. Devlin

(57) ABSTRACT

This invention relates to screening assay methods that can be applied to broad members of the protein kinase gene family and are useful in the detection and evaluation of kinase inhibitors.

7 Claims, 4 Drawing Sheets

METHODS FOR DETERMINING PHOSPHORYLTRANSFERASE ACTIVITY USING ADENOSINE 5'-TRIPHOSPHATE (ATP)-GAMMA-S

FIELD OF THE INVENTION

This invention relates generally to novel screening assay methods that can be applied to broad members of the protein kinase gene family and are useful in the detection and evaluation of kinase inhibitors.

BACKGROUND OF THE INVENTION

Protein kinases play a critical role in the regulation of virtually all aspects of cellular regulation and comprise one of the most active areas of research in the pharmaceutical industry today. The 522 protein kinase domains in the human genome may provide tremendous opportunities for developing new drugs for untreated disease, and the development of protein kinase inhibitors has increasingly become a major focus for the pharmaceutical industry. Protein kinase inhibitors have been reported to be useful in the treatment of numerous diseases including cancer, inflammatory and immunological diseases. See for example I. K. Mellinghoff and C. L. Sawyers, Kinase Inhibitor Therapy in Cancer, 14(12):1-11, 2000; J. Dumas, Growth factor receptor kinase inhibitors: recent progress and clinical impact, Current Opinion in Drug Discovery & Development, 4(4):378-89, 2001; J. Dumas, Protein kinase inhibitors: emerging pharmacophores, 1997-2000, Expert Opinion on Therapeutic Patents, 11(3):405-429, 2001; D. H. Williams and T. Mitchell, Latest developments in crystallography and structure-based design of protein kinase inhibitors as drug candidates, Current Opinion in Pharmacology, 2(5):567-73, 2002; S. B. Noonberg and C. C. Benz, Tyrosine kinase inhibitors targeted to the epidermal growth factor receptor subfamily: role as anticancer agents, Drugs, 59(4):753-67, 2000; S. Brunelleschi, L. Penengo, M. M. Santoro and G. Gaudino, Receptor tyrosine kinases as target for anti-cancer therapy, Current Pharmaceutical Design, 8(22):1959-72, 2002; P. G. Goekjian and M. R. Jirousek, Protein kinase C in the treatment of disease: signal transduction pathways, inhibitors, and agents in development, Current Medicinal Chemistry, 6(9):877-903, 1999; A. Gordon, The increasing efficacy of breast cancer treatment, Clinical Oncology (Royal College of Radiologists), 9(5):338-42, 1997.

While this large gene family represents a rich source of new drug targets, developing assays used to determine compound affinity can be highly problematic. Current high throughput screening assays for protein kinase inhibitors measure the incorporation of phosphate into a protein or peptide substrate. The most established method for assaying protein kinase inhibitors is a radiometric assay in which the gamma phosphate of ATP is labeled with either $^{32}$P or $^{33}$P. When the kinase transfers the gamma phosphate to the hydroxyl of the protein substrate during the phosphoryltransferase reaction the protein becomes covalently labeled with the isotope. The protein is removed from the labeled ATP and the amount of radioactive protein is determined. This assay is still the gold standard for quantitative protein kinase assays. Adaptation of this assay into a high throughput format is problematic due to the labor intensive separation steps and the large amounts of radioactivity that are used.

An alternative radiometric assay that is capable of higher throughput is the SPA or scintillation proximity assay (Amersham International). In this assay scintillant impregnated beads emit light when the labeled substrate is bound to the bead. This assay is limited by the level of radioactivity and the efficiency of the peptide substrate.

Techniques using fluorescence polarization to measure either protein kinase activity or inhibitor binding rely on a labeled antibody or peptide substrate. In these assays the enzyme transfers the gamma phosphate of ATP to a protein or peptide substrate. This activity is monitored by detecting the phospho-peptide by such means as an antibody. The binding of the antibody to the phospho-peptide will slow the free rotation of the peptide in solution and, therefore, a polarization signal from the product of the catalytic reaction can be detected. Examples include Burke et al., US 2001/0004522 A1 or T. C. Turek et al., Analytical Biochemistry, 299 (1), 25-53, 2001.

Many of the non-radioactive assays mentioned above use antibodies that recognize the product of the kinase reaction, i.e. a phospho-peptide. The binding assays use antibodies detected with enzyme-catalyzed luminescent readout. These methods are limited by reagent availability, well coating, and multiple wash incubation steps. Most importantly, however, antibody-based techniques for serine/threonine kinases require a specialized antibody for each kinase substrate. This requires that the phosphorylation site is known and that a antibody can be generated to that site. This increases the time, risk, and expense of assay generation. Additionally, only one phosphorylation site on a protein can be measured while, in practice, multiple sites on target proteins can be phosphorylated by a single kinase.

Another non-radioactive assay method utilizes the ATP-dependent activity of commercially available firefly luciferase. For example, U.S. Pat. No. 6,599,711 describes a method for measuring protein kinase activity by using bioluminescence to measure the change in ATP concentration following the phosphorylation of a protein kinase substrate in the presence of the protein kinase and ATP. The amount of light emitted by luciferase is directly proportional to the residual ATP following the kinase reaction. A tremendous advantage of this approach is that it does not require specialized detection reagents for each kinase thereby allowing screening panels to be set up in a single, common format.

We, and others, have shown that many protein kinases exhibit ATP hydrolysis in the absence of a protein acceptor substrate (New Tools for Screening Kinases: A Comparative Study", The Society for Biomolecular Screening 9$^{th}$ Annual Conference, 2003, Portland, Oreg., Sep. 21-25, 2003, Kashem, M. A., Yingling, J., Nelson, R. M. and Homon, C. A.). In this case water acts as the terminal phosphate acceptor rather the hydroxyl of an amino acid as is traditionally the case in a phosphotransferase reaction. This ATPase activity is termed "intrinsic ATPase". Assay formats based on ATP depletion will measure both phosphotransferase activity to protein and water. A drawback to the approach is that non-kinase ATPases that may be present as contaminants to the enzyme preparation will also show activity that could mistakenly be assigned to the protein kinase. Another potential complication is many protein kinases are assayed as enzymatic cascades wherein an upstream kinase phosphorylates and activates a downstream kinase. In a enzyme reaction in which multiple protein kinases are present, total ATP consumption is the sum of the activity of both the kinase of interest and the substrate kinase. Specific inhibition of the upstream kinase is likely to be obscured by the activity of the substrate kinase resulting in missed compounds which are active against the kinase of interest. Furthermore, if a kinase exhibited intrinsic ATPase activity equal or greater than its substrate-dependent phosphoryltransferase activity, identification of inhibitors that do not compete with ATP binding would not be possible. Very little has been published about the ATPase activity of protein kinases. In any case, it has never been considered a "problem" which anyone has tried to solve for quantification of ATP to determine kinase activity.

SUMMARY OF THE INVENTION

This invention describes methods that specifically measure kinase-mediated phosphoryltransfer of the gamma-phosphate of a non-hydrolyzable analog of ATP, ATP-γ-S. These methods effectively eliminate any interference which results from trace amounts of contaminating ATPases. Additionally, these methods can render a kinase reaction completely substrate-dependent, even when the kinase exhibits intrinsic ATPase activity.

DETAILED DESCRIPTION OF THE INVENTION

Figure 1:
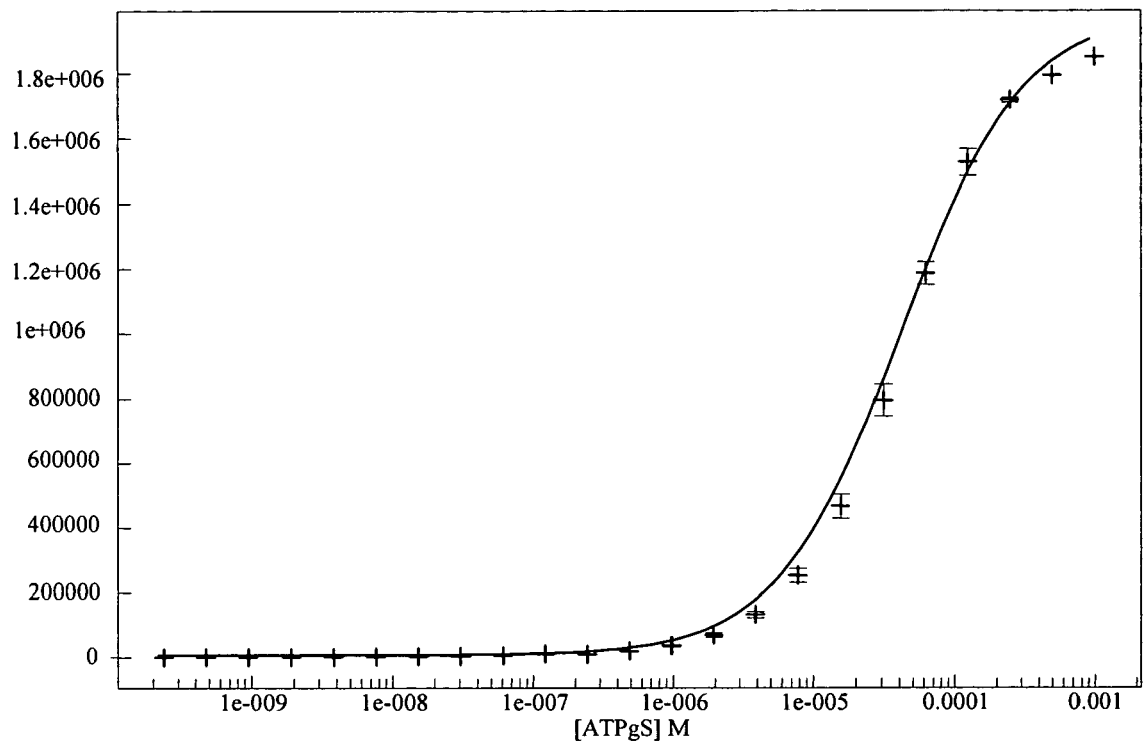
FIG. 1 illustrates the determination of the $K_m$(ATP-γ-S) for luciferase. ATP-γ-S (23 concentrations over the range of 1 mM to 238 pM) were added to the Kinase-Glo™ Data were quantified using the luminescence mode of an LJL Analyst after 15 minutes incubation. RLU is relative light unit. + is observed value. − is predicted value.

Most technologies used in drug discovery screening efforts for protein kinase inhibitors have required separation of products and reactants. The luciferase-based reagents marketed to date have eliminated this requirement. However, the use of ATP in these technologies has presented the unforeseen problems associated with 1) intrinsic ATPase activity of some protein kinases and 2) contaminating ATPases in the protein preparations. These effects went undetected in traditional technologies used in protein kinase drug discovery efforts.

Classically, protein kinases exist as components of activation cascades, wherein phosphorylation of one protein kinase by another upstream protein kinase results in its activation. The activated protein kinase might, in turn, activate another protein kinase. In assays where both the primary enzyme of interest and its substrate are protein kinases, several complicating situations might arise. Since assays are typically designed so that there is a large molar excess of substrate compared to enzyme (1:100 to 1:1000), even modest intrinsic ATPase activity of the substrate protein will result in a large portion of the total ATP consuming activity remaining uninhibited even in the face of complete inhibition of the primary enzyme. In addition to the intentional molar excess of substrate over enzyme, activation of the substrate, which would occur during the assay as a result of its phosphorylation, would further increase the fractional ATP consumption attributed to the intrinsic ATPase activity of the substrate. This would further reduce the likelihood of identifying kinase inhibitors. The technique we have developed allows us to measure exclusively the phosphoryltransferase activity of the primary enzyme without interference due to the intrinsic ATPase activity of the substrate kinase.

A problem intrinsic to measuring protein kinase activity through ATP reduction is the presence of non-kinase ATPase activities contaminating the assay system. ATPases are very prevalent in cell extracts and can persist throughout the purification of the protein kinase. In these cases, trace contamination by ATPases might prevent the use of current technologies which monitor ATP levels. Extensive purification to remove these contaminants is expensive, time-consuming, labor-intensive and often, even when successful, results in final protein yields which are insufficient to perform a screening campaign. In addition, contaminating ATPase could arise from either the enzyme or substrate preparations. Given the high concentrations of substrate relative to enzyme typically present, it can be very difficult to provide a protein substrate preparation without trace levels of ATPase activity. The present invention eliminates the need for enzyme preparations devoid of contaminating ATPases. As before, the invention exploits the unique ability of kinases to use ATP-γ-S in phosphoryltransferase reactions.

The invention described herein eliminates the problems discussed above through the use of ATP-γ-S (Adenosine 5'-[γ-thio]triphosphate) which is not a substrate for ATPases.

The primary advantage of this invention over existing techniques lies in the ability of ATP-γ-S to distinguish between phosphoryltransferase activity of protein kinases and ATP hydrolysis mediated by the protein kinase itself or a contaminating ATPase.

In one embodiment, the invention relates to a method for measuring protein kinase activity comprising: (a) providing a first solution comprising a protein kinase and ATP-γ-S; (b) providing a second solution comprising the same protein kinase of the solution of step (a), ATP-γ-S and a substrate capable of being phosphorylated by said protein kinase; (c) incubating each of the solutions to allow the phosphorylation reaction to proceed; (d) measuring the amount of the ATP-γ-S remaining in the first solution and the amount of the ATP-γ-S remaining in the second solution; and (e) comparing the amount of the ATP-γ-S remaining in the first solution to the amount of the ATP-γ-S remaining in the second solution to determine the activity of the protein kinase.

In an embodiment, each solution of step (a) and (b) of the method for measuring protein kinase activity can be allowed to incubate for time intervals up to eight hours, preferably up to six hours, more preferably up to four hours, and the amount of the ATP-γ-S remaining in the first solution and in the second solution is determined for each interval.

Another embodiment of the invention relates to a method for identifying a compound which modulates the activity of a protein kinase comprising: (a) a first solution comprising a protein kinase, ATP-γ-S, a substrate capable of being phosphorylated by said protein kinase, and a test compound; (b) a second solution comprising a protein kinase, ATP-γ-S and a substrate capable of being phosphorylated by said protein kinase; (c) a third solution comprising ATP-γ-S, a substrate capable of being phosphorylated by said protein kinase, and a test compound; (d) incubating each of the solutions of steps (a), (b), and (c); and (e) comparing the amount of the ATP-γ-S remaining in the first, second and third solutions to determine whether the compound modulates the activity of the protein kinase.

In an embodiment, each of the solutions of step (a), (b), and (c) of the method for identifying a compound which modulates the activity of a protein kinase are incubated for 10 minutes to six hours, preferably 20 minutes to four hours, more preferably 30 minutes to two hours.

In step (b) of the methods of the invention, the substrate can be a protein kinase other than the protein kinase of step (a).

The concentration of ATP-γ-S may be determined by methods known in the art, including but not limited to bioluminescence reaction or radiometric assays. A bioluminescence reaction can include, for example, a luciferin and a luciferase wherein the luciferin emits light in the presence of the luciferase and ATP-γ-S.

A compound which modulates the activity of the protein kinase may inhibit or enhance the activity.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various patent applications and publications are cited herein, the disclosures of which are incorporated by reference in their entireties.

EXAMPLES

Determination of Km(ATP-γ-S) for Luciferase

It has been reported (B. Ortiz et al., Eur. J. Biochem, 1993, 212, 263-270) that ATP-γ-S is a substrate for luciferase. To confirm this, 23 concentrations of ATP-γ-S over the range of 1 mM to 238 pM (2-fold dilutions between concentrations) were added to the Kinase-Glo™ reagent (reconstituted according to package instructions) then diluted 1:6 (final) into the assay. The assay buffer consisted of: 50 mM HEPES, pH 7.5, 50 mM KCl, 10 mM MgCl2, 100 μM sodium orthovanadate, 0.01% CHAPS and 0.5 mM DTT. The assay plate used was the Greiner Lumitrac 200. Data were quantified using the luminescence mode of an LJL Analyst after 15 minutes incubation.

The results shown in FIG. 1 confirm that ATP-γ-S is a substrate for luciferase and illustrate the $K_m$ of ATP-γ-S for luciferase.

ATP Consumption in Absence of Acceptor Substrate

Figure 2:
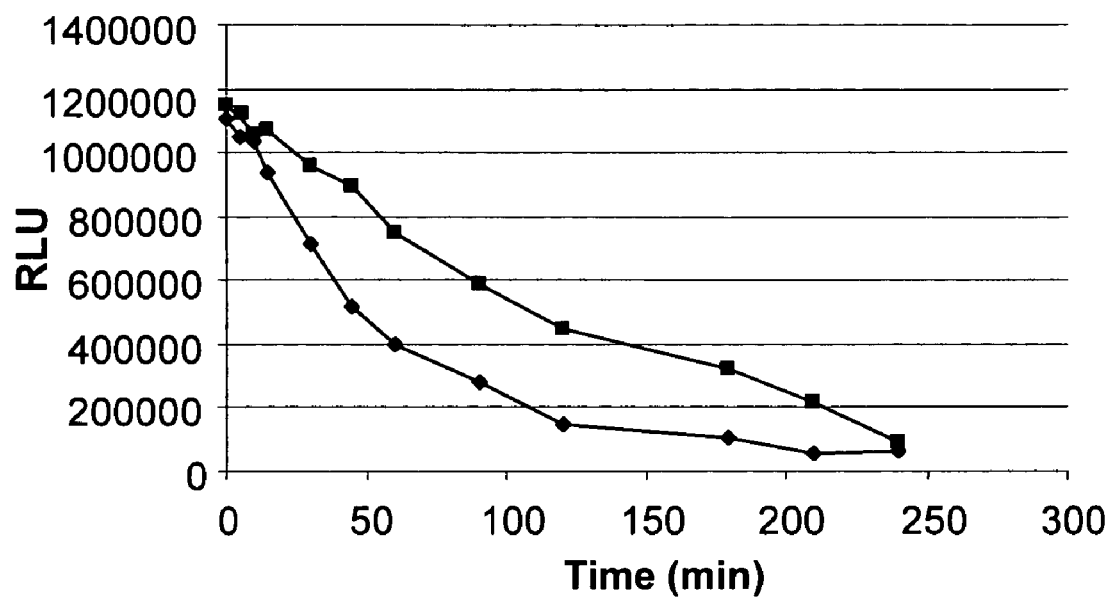
FIG. 2 illustrates the initial observation of ATP consumption by MKK3 in the absence of p38, the acceptor substrate. MKK3 (10 nM) was added to ATP (300 nM) for the times indicated and reactions were terminated by the addition of the Kinase-Glo™ reagent. Data were quantified using the luminescence mode of an LJL Analyst after 15 minutes incubation. Also shown is the reaction in the presence of substrate, 150 nM p38. RLU is relative light unit. -■- MKK3 alone. -♦- MKK3 in the presence of p38.

FIG. 2 illustrates the initial observation of ATP consumption by MKK3 in the absence of p38, the acceptor substrate. At this point it was unclear whether the activity was due to intrinsic ATPase activity of MKK3 or a contaminating ATPase. This experiment was performed in the same assay plates using the same buffers as the $K_m$ (ATP-γ-S) and data were quantified identically. MKK3 (10 nM) was added to 300 nM ATP for the times indicated and reactions were terminated by the addition of the Kinase-Glo™ reagent, reconstituted and used according to package instructions. Also shown is the reaction in the presence of p38 (150 nM). Clearly, a significant portion of the consumption is due to the intrinsic ATPase activity of the MKK3 or a contaminating ATPase and not due to the phosphoryltransferase activity of MKK3.

Elimination of ATP Consumption

Figure 3:
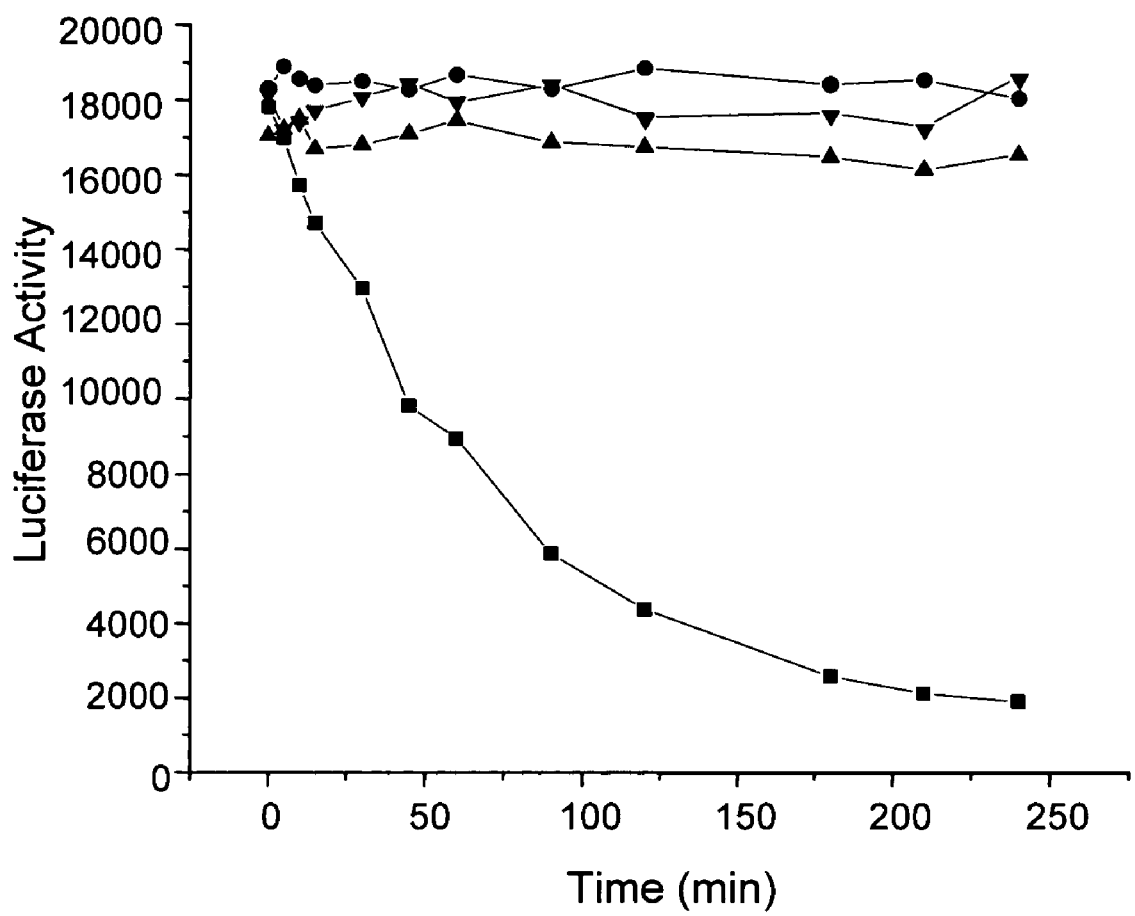
FIG. 3 illustrates the elimination of ATP consumption (whether intrinsic to MKK3 or from a contaminant) in the absence of p38, the acceptor substrate. This experiment was conducted according to the methods used in FIG. 2 except for the substitution of 300 nM ATP-γ-S for the ATP. -■- MKK3 in the presence of p38. -▲- MKK3 alone. -●- p38 alone. -▼- Control without MKK3 or p38.

FIG. 3 illustrates the elimination of ATP consumption (whether intrinsic to MKK3 or from a contaminant) in the absence of p38, the acceptor substrate. This experiment was conducted according to the methods used in FIG. 2 except for the substitution of 300 nM ATP-γ-S for the ATP.

ATP consumption is shown in FIG. 3 for MKK3 in the presence of substrate p38, MKK3 alone, p38 alone and in the absence of both MKK3 and p38 (control). As seen in FIG. 3, ATP was only consumed when MKK3 and its substrate p38 were present and phosphorytransferase took place. With either MKK3 or p38 alone, there was no consumption of ATP (compared to control) and thus no intrinsic ATPase activity was detected when the reaction was run in the presence of ATP-γ-S.

The use of ATP-γ-S in place of ATP could be applied to luciferase assays with other classes of proteins for which ATP is consumed as a primary substrate or required cofactor. These could include the membrane-base ATPases such as Na+-K+ ATPase, metabolic enzymes such as pyruvate kinase, or nucleic acid modifying enzymes such as T4 polynucleotide kinase. For example, adenosine 5'-triphosphatases (ATPases) are extremely prevalent enzymes which also cleave ATP to ADP.

Inhibition of Phosphoryltransferase Activity

Figure 4:
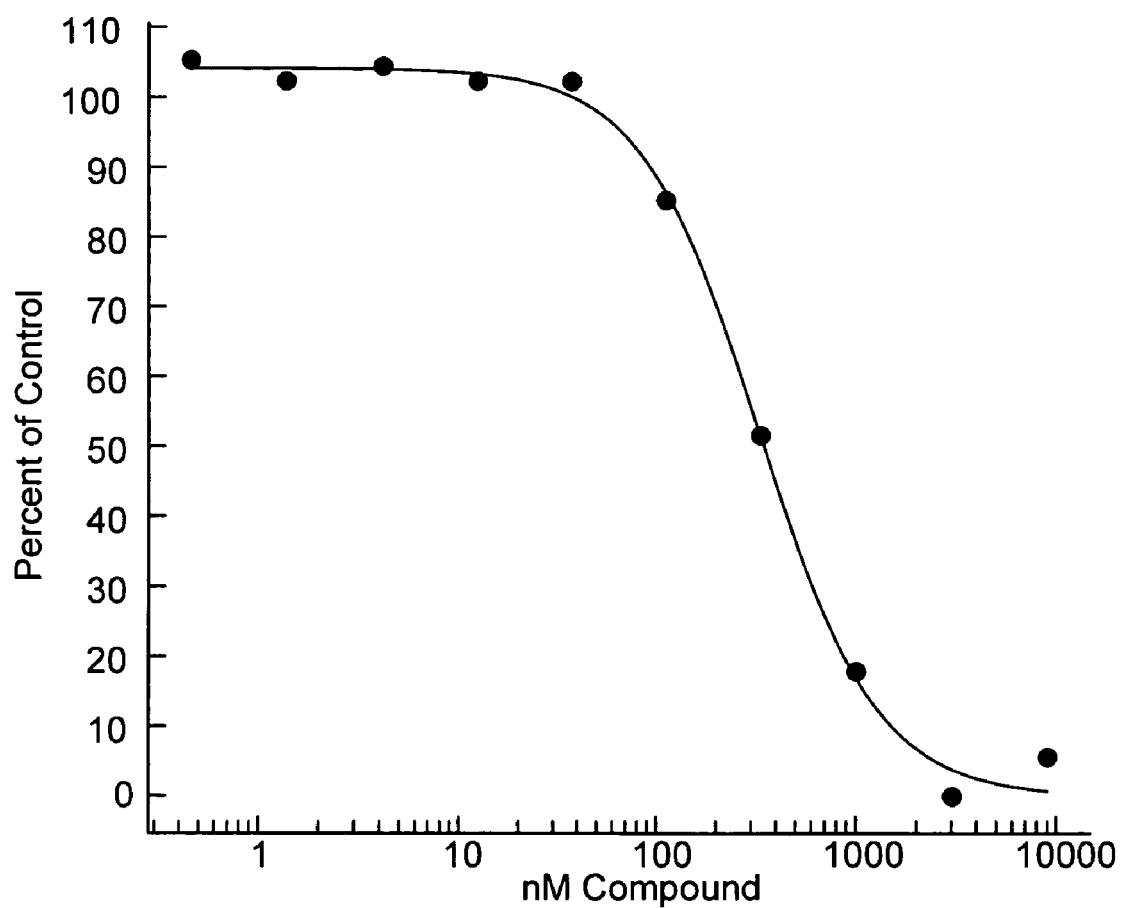
FIG. 4 illustrates results for an assay using ATP-γ-S and measuring inhibition by a test compound of the phosphoryltransferase activity of a kinase, MKK3. $IC_{50}$ (inhibitory concentration 50%) was 330 nM.

FIG. 4 illustrates results for an assay using ATP-γ-S and measuring inhibition by a test compound of the phosphoryltransferase activity of a kinase, MKK3.

The following example describes an assay for measuring inhibition by test compounds of the phosphoryltransferase activity of a kinase, MKK3. The substrate which was phosphorylated in the assay is p38. The activity was measured using the Kinase-Glo technology (Cambrex # V6714) which measures ATP-γ-S consumption via its effect on firefly luciferase activity. Data were generated using Greiner Lumitrac 200 microtiter plates (#781075). The assay buffer consisted of: 50 mM HEPES, pH 7.5, 50 mM KCl, 10 mM MgCl2, 100 μM sodium orthovanadate, 0.01% CHAPS and 0.5 mM DTT. Assay assembly was as follows: 20 μL of 20 nM MKK3 was added to an empty Lumitrac 200 plate. Ten microliters of 12 μg/mL compound in 2.4% DMSO was added, followed by 10 μL of a solution containing 600 nM p38 and 1.2 μM ATP-γ-S. The reaction (final concentrations: 10 nM MKK3; 3 μg/mL compound in 0.6% DMSO; 150 nM p38 and 300 nM ATP-γ-S) was incubated for ninety minutes. Controls were determined by the activity measured in the same reaction mixture without the MKK3 and in the same reaction mixture with MKK3 but without test compound. Following the incubation, 40 μL of the Kinase-Glo reagent (reconstituted according to package instructions, then diluted 1:5 in MKK3 complete assay buffer) was added. Plates were incubated for an additional 15 minutes before being quantified using an LJL Analyst in luminescence mode. Activity Base Software was used for data reduction.

Data are expressed as percent of control of phosphoryl-transferase activity for each concentration of test compound used and were calculated as follows:

$$\text{Percent of control} = (R_T - R_b)/(R_c - R_b) \times 100$$

$R_t$ is the luminescence readout for the reaction with test compound at a given concentration in the presence of MKK3.

$R_b$ is the luminescence readout for the reaction in the presence of test compound but no MKK3 (blank)

$R_c$ is the luminescence readout for the reaction in the presence of MKK3 but no test compound (control)

As shown in FIG. 4, IC$_{50}$ (inhibitory concentration 50%) was 330 mM.

What is claimed is:

1. A method for measuring protein kinase activity comprising:
   (a) providing a first solution comprising a protein kinase and ATP-γ-S;
   (b) providing a second solution comprising the same protein kinase of the solution of step (a), ATP-γ-S and a substrate which can be phosphorylated by said protein kinase;
   (c) incubating each of the solutions such that a phosphorylation reaction occurs;
   (d) measuring an amount of the ATP-γ-S remaining in the first solution and an amount of the ATP-γ-S remaining in the second solution; and
   (e) comparing an amount of the ATP-γ-S remaining in the first solution to an amount of the ATP-γ-S remaining in the second solution to determine the activity of the protein kinase.

2. The method of claim 1 wherein the amount of the ATP-γ-S is determined using a bioluminescence reaction.

3. The method of claim 1 wherein the amount of the ATP-γ-S is determined using a radiometric assay.

4. The method of claim 2 wherein the bioluminescence reaction is carried out using a luciferin and a luciferase wherein the luciferin emits light in the presence of the luciferase and the ATP-γ-S.

5. The method of claim 1 wherein the substrate being phosphorylated is a protein kinase other than said protein kinase of the first solution.

6. The method of claim 1 wherein the first solution and the second solution are incubated for time intervals up to four hours and the amount of the ATP-γ-S remaining in the first solution and in the second solution is determined for each time interval.

7. A method for measuring protein kinase activity comprising:
   (a) providing a first solution consisting essentially of a protein kinase and ATP-γ-S;
   (b) providing a second solution comprising the same protein kinase of the solution of step (a), ATP-γ-S and a substrate which can be phosphorylated by said protein kinase;
   (c) incubating each of the solutions such that a phosphorylation reaction occurs;
   (d) measuring an amount of the ATP-γ-S remaining in the first solution and an amount of the ATP-γ-S remaining in the second solution; and
   (e) comparing an amount of the ATP-γ-S remaining in the first solution to an amount of the ATP-γ-S remaining in the second solution to determine the activity of the protein kinase.

* * * * *